(12) United States Patent
Harvey et al.

(10) Patent No.: US 8,227,651 B1
(45) Date of Patent: Jul. 24, 2012

(54) HIGH DENSITY RENEWABLE FUELS BASED ON THE SELECTIVE DIMERIZATION OF PINENES

(75) Inventors: Benjamin G. Harvey, Ridgecrest, CA (US); Michael E. Wright, Tremonton, UT (US); Roxanne L. Quintana, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 281 days.

(21) Appl. No.: 12/550,973

(22) Filed: Aug. 31, 2009

(51) Int. Cl.
*C07C 13/28* (2006.01)
(52) U.S. Cl. .............. 585/362; 585/14; 585/16; 585/20; 585/360; 585/361; 44/300
(58) Field of Classification Search .................... 585/16, 585/14, 362, 360, 361
See application file for complete search history.

(56) References Cited

U.S. PATENT DOCUMENTS

| | | | | |
|---|---|---|---|---|
| 4,052,549 A | * | 10/1977 | Booth | 526/237 |
| 4,165,301 A | * | 8/1979 | Wiegers et al. | 512/3 |
| 4,922,047 A | * | 5/1990 | Chen et al. | 585/12 |
| 5,723,709 A | * | 3/1998 | Phillips et al. | 585/20 |
| 5,762,696 A | * | 6/1998 | Jordan | 106/226 |
| 5,847,247 A | * | 12/1998 | Conte et al. | 585/20 |
| 6,566,570 B1 | * | 5/2003 | Bergstrom et al. | 585/361 |

* cited by examiner

*Primary Examiner* — Ellen McAvoy
(74) *Attorney, Agent, or Firm* — Brian F. Drazich; Charlene A. Haley

(57) ABSTRACT

An effective method for producing high density fuel candidates from pinenes is provided. MMT-K10 is an efficient catalyst for the reaction, although significant amounts of p-cymene and camphene produced as byproducts limit the overall yield to about 80%. Nafion is also an excellent catalyst for pinene dimerization and was capable of producing dimers in up to 90% yield. Pinene dimers synthesized with these heterogenous catalysts have a density and net heat of combustion comparable to JP-10. It is emphasized that this abstract is provided to comply with the rules requiring an abstract that will allow a searcher or other reader to quickly ascertain the subject matter of the technical disclosure. It is submitted with the understanding that it will not be used to interpret or limit the scope of the claims.

3 Claims, 1 Drawing Sheet

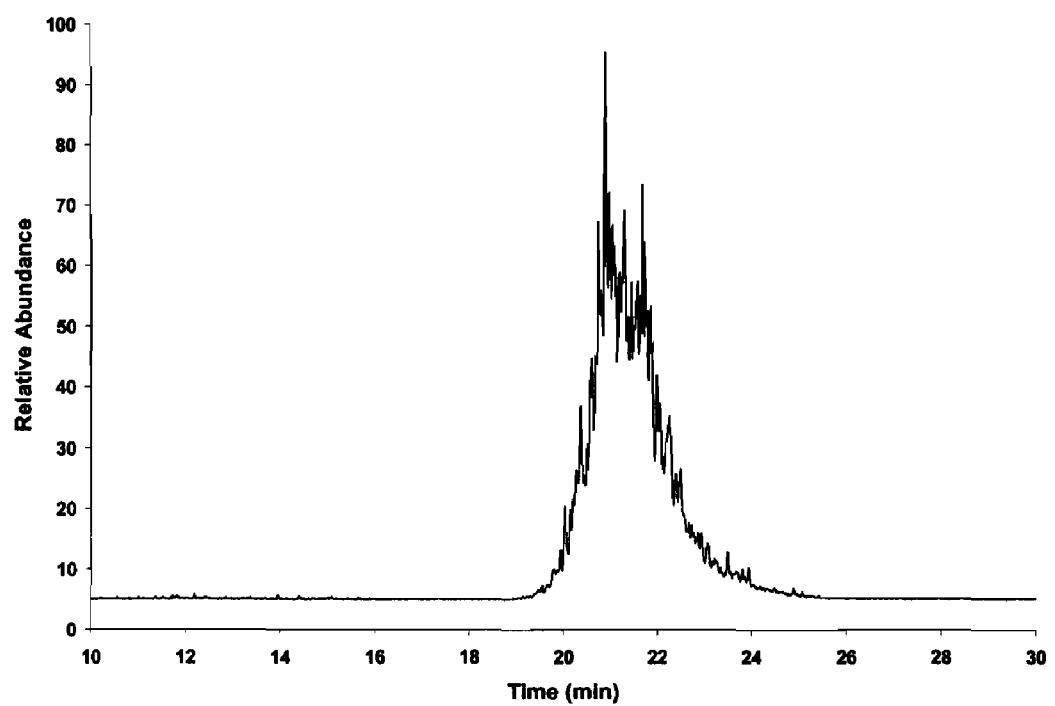

HIGH DENSITY RENEWABLE FUELS BASED ON THE SELECTIVE DIMERIZATION OF PINENES

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

Disclosed here is the synthesis of high density fuels from renewable sources. These fuels which can be produced in the United States, reducing dependence on foreign oil, have potential for use in rocket engines and in a wide variety of jet or turbine engines.

The synthesis of high density fuels derived from renewable sources is novel. Such fuels have much higher densities and net heating values than more conventional renewable fuels including biodiesel and bioethanol. Further, these fuels have properties that are competitive with specialized conventional petroleum based fuels.

BACKGROUND OF THE INVENTION

The efficient production of fuels and plastics from renewable sources is one of the key technological challenges of this century (Ragauskas, A. J.; Williams, C. K.; Davison, B. H.; Britovsek, G.; Cairney, J.; Eckert, C. A.; Frederick, W. J.; Hallet, J. P.; Leak, D. J.; Liotta, C. L.; Mielenz, J. R.; Murphy, R.; Templer, R.; Tschaplinski, T. *Science* 2006 311 484-489). Conventional, petroleum based, high density tactical fuels such as JP-10 and RJ-5 (Diagram 1, exo-tetrahydrodicyclopentadiene and norbornadiene dimers, respectively) will be particularly hard to replace given their high densities of 0.94 g/mL and 1.08 g/mL, respectively. In the case of RJ-5 (perhydroinorbornadiene), significant ring strain contributes to a high heat of combustion (Table 1). Although bulk agricultural waste products such as cellulose and lignin are often targeted as feedstocks for the production of renewable fuels, even saturated hydrocarbon fuels which have previously been prepared from the dehydration products of cellulose derived alcohols have a density of only 0.78 g/mL, (Wright, M. E.; Harvey, Benjamin G.; Quintana, R. *Energy and Fuels* 2008, 22, 3299) while JP-5 which contains aromatic compounds typically has a density of 0.83 g/mL. These lower densities are reflected in the volumetric heating value of these fuels, with cellulose based jet or turbine fuels and JP-5 capable of producing only 34.3 MJ/L and 34.8 MJ/L, respectively, compared to 39.6 MJ/L for JP-10 and 44.9 MJ/L for RJ-5 (Wright, M. E.; Harvey, Benjamin G.; Quintana, R. *Energy and Fuels* 2008, 22, 3299) (Burdette, G. W.; Lander, H. R.; McCoy, J. R. *J. Energy* 1978, 2, 289-292).

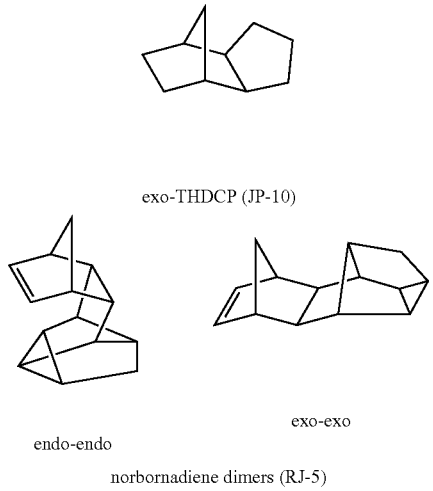

Diagram 1. Structures of high density fuels exo-THDCP (JP-10)

endo-endo          exo-exo norbornadiene dimers (RJ-5)

TABLE 1

Selected data for high density military tactical fuels

|  | JP-5 | JP-10 | RJ-5 |
| --- | --- | --- | --- |
| Heating Value, MJ/L | 34.8 | 39.6 | 44.9 |
| (Btu/gal) | (125,000) | (142,000) | (161,000) |
| Freezing Point, K | <227 | <194 | >255 |
| Specific Gravity (g/mL) | 0.83 | 0.94 | 1.08 |

In addition to having an outstanding volumetric heating value, tactical fuels must have low freezing points for use at high altitudes and in cold climates. These restrictions have limited the use of RJ-5 as a standalone fuel notwithstanding its impressive heating value. Based on these challenging requirements, it is clear that specialized, readily available, and reactive renewable feedstocks will be necessary to produce tactical fuel replacements. α- and β-pinene (Diagram 2) are versatile natural products that are produced by a wide variety of trees and other plant life. They have industrial applications as solvents, pharmaceutical synthons, and in the production of cosmetics and perfumes. Natural turpentine is composed primarily of α- and β-pinene (Coppen, J. J. W.; Hone, G. A. *Gum Naval Stores: Turpentine and Rosin from Pine Resin*, FAO: Rome 1995). Terpenes have a rich history in the use of pharmaceuticals and have been used themselves as therapeutic agents (Monteiro, J. L. F.; Veloso, C. O. *Topics in Catalysis* 2004, 27, 169) (Wiegers, W. J.; Hall, J. B.; Hill, I. D.; Novak, R. M.; Schmitt, F. L.; Mookhersee, B. D.; Shu, C.; Schreiber, W. L. U.S. Pat. No. 4,165,301 1979). Due to their compact structures and reactive olefin functionalities, pinenes have significant potential as feedstocks for high density renewable fuels (Harvey, B. G.; Wright, M. E.; Quintana, R. L. *Preprints of Symposia-ACS Div. Fuel Chem.* 2009 54 305-306) (Filley, J.; Miedaner, A.; Ibrahim, M.; Nimlos, M. R.; Blake, D. M. *J. Photochem. Photobio. A* 2001 139, 17-21). Both molecules have bicyclic structures incorporating cyclobutanes that possess on the order of 100 kJ/mol of ring strain (Joshi, R. M. *J. Macrom. Sci. Part A* 1972 6, 595-629). This energy is released upon combustion resulting in a higher heat of combustion than unstrained or linear molecules with similar molecular weights. The volumetric heat of combustion can be further improved through dimerization which significantly increases the density of the mixture. In industry, the dimerization of olefins is often carried out with environmentally unfavorable catalysts such as sulfuric or hydrofluoric acid. These catalysts are corrosive, dangerous to work with, and their use Diagram 2. Structures of α- and β-pinene

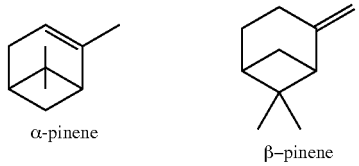

results in the production of large amounts of waste that must be either treated or recycled, resulting in significant energy demands and higher costs. In contrast, the use of solid acid catalysts provides several advantages over conventional liquid acid systems. For example, these heterogeneous catalysts are typically much less corrosive, safer to work with, easier to separate, and more easily recycled than liquid acid systems (Sheldon, R. A.; Downing, R. S. *Applied Catalysis A* 1999 189, 163-183) (Kumar, P.; Vermeiren, W.; Dath, J.; Hoelderich, W. F. *Energy Fuels* 2006 20, 481-487).

Dimerization of α- and β-pinene has been reported utilizing both Bronsted acid catalysts such as phosphoric acid (Phillips, C. F.; Booth, J. W. U.S. Pat. No. 5,723,709 1998) and Lewis acid catalysts such as $BF_3$ (Chapaton, T. J.; Capehart, T. W.; Linden, J. L. *Tribology Transactions* 2006 49, 454-472) (Chapaton, T. J.; Capehart, T. W.; Linden, J. L. U.S. Pat. No. 6,828,283 2004). Upon hydrogenation, these dimers have been utilized for an array of end uses, from beauty products to traction fluids. Unfortunately, previous studies have revealed complicated product distributions and have provided little evidence as to the structures of the dimers. To selectively produce dimer mixtures with potential uses as high density renewable fuels utilizing more environmentally friendly catalysts, or at least catalysts potentially less environmentally damaging than conventional liquid acid systems, we have studied the reactions of β-pinene with acidic heterogeneous catalysts including Montmorillonite K10 (MMT-K10), Amberlyst-15, and Nafion NR-50.

BRIEF DESCRIPTION OF THE DRAWINGS

FIG. 1 of the drawings is a GC/MS chromatogram of a product mixture.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS

High density fuel candidates have been synthesized in up to 90% yield from β-pinene, a renewable strained bicyclic compound derived from wood and plant sources. These novel synthesis are based on heterogeneous acidic catalysts (also referred to as heteropolyacidic catalysts) including Montmorillonite-K10 and Nafion® NR-50 which promote selective isomerization and dimerization of pinenes under moderate conditions (100° C., atmospheric pressure). Montmorillonite clays have been used as catalysts for number of organic reactions and offer several advantages over classical acids. For example, the strong acidity, non-corrosive properties, mild reaction conditions, high yields, selectivity, low cost, and the ease of setting and working-up. The mesoporous Montmorillonite clays, which are dioctahedral phyllosilicates, are composed of hydrated sodium calcium aluminium magnesium silicate hydroxide $(Na,Ca)_{0.33}(Al,Mg)_2(Si_4O_{10})$ $(OH)_2.nH_2O$, with an octahedral layer ($AlO_6$ units) sandwiched between two tetrahedral layers ($SiO_4$ units). Potassium, iron, and other cations are common substitutes. These clays typically have a surface area of 220-270 $m^2/g$. Montmorillonite-K10 is a strong Bronsted and Lewis acidic catalyst shown to be a highly active catalyst for dimerization but is also active in the ring opening of β-pinene followed by dehydrogenation to produce p-cymene. This limited the yield of dimer to about 75%. Nafion catalysis was capable of producing dimers in up to 90% yield but was less active than the acidic clay. Amberlyst-15, a common industrial catalyst had very poor activity and conversion even at 150° C.

The dimer mixtures were upgraded through hydrogenation over $PtO_2$ and fractional distillation. The synthesized fuels have a density of about 0.94 g/cc, and a net volumetric heating value of about 39.5 MJ/L (~141,745 BTU/gal). These values are nearly identical to those of the widely used tactical fuel JP-10 (which is primarily composed of exo-tetrahydrodicyclopentadiene), suggesting that these renewable fuels may have applications for rocket propulsion.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments which are illustrated schematically in the accompanying drawings and in the appended claims.

β-pinene Dimerization

Note of caution: the dimerization reaction is very exothermic, particularly when MMT-K10 is used as the catalyst. Runaway reactions can occur with both MMT-K10 and Nafion, especially with concentrated solutions or in the absence of a suitable heat sink Slow addition of β-pinene to a refluxing reaction mixture at 100° C. was determined to be the safest method of addition. In a typical procedure, the solid acid catalyst (100 mg Nafion or 500 mg MMT-K10) was slurried in 10 mL of n-heptane under a nitrogen atmosphere and heated to reflux. β-pinene (35 g) was then added dropwise to the slurry and the reflux was maintained with external heat for the remainder of the reaction; additional reactions were conducted over a range of temperatures from 0° C. up to the reflux temperature of β-pinene. Dimer mixtures were hydrogenated with 1 wt % $PtO_2$ under 1-2 psig of hydrogen for a period ranging from about 12 hours to about 24 hours. Subsequent distillations were carried out under reduced pressure (4 mm Hg).

TABLE 2

Catalysts for the Dimerization of β-pinene

| Catalyst | Temperature | Time | Products |
| --- | --- | --- | --- |
| MMT-K10 | 0-30° C. | 4 h | isomers |
| MMT-K10 | 100° C. | 1 h | dimer/isomers |
| MMT-K10 | 150° C. | 1 h | dimer/trimer/isomers |
| Amberlyst-15 | ambient | 24 h | NR |
| Amberlyst-15 | 150° C. | 3 h | isomers |

TABLE 2-continued

Catalysts for the Dimerization of β-pinene

| Catalyst | Temperature | Time | Products |
|---|---|---|---|
| Nafion | ambient | 24 h | NR |
| Nafion | 100° C. | 6 h | dimer/isomers |
| Nafion | 150° C. | 2 h | dimer/isomers/trimer |
| $H_2SO_4$ (98%) | 0° C. | 10 min | polymer |
| $H_2SO_4$ (50%) | 0° C. | 10 min | polymer |

Nafion® NR-50 (Aldrich) was precipitated from a 5% water/alcohol dispersion by addition of dichloromethane ($CH_2Cl_2$) and ether, followed by filtration and drying under vacuum (4 Torr) at ambient temperature (adapted from Kim, T. K.; Kang, M.; Choi, Y. S.; Kim, H. K.; Lee, W.; Chang, H.; Seung, D. *J. Power Sources* 2007 165, 1-8). The MMT-K10 (Aldrich) and dry Amberlyst-15 (Aldrich) were used directly from the bottle. (1S)-(−)-β-pinene (Aldrich) typically was used without further purification, or after an extended storage time, it was distilled from $CaH_2$ under a nitrogen atmosphere. Product mixtures were analyzed with an Agilent 6890-GC/5973-MS mass spectrograph to determine chemical compositions. The density of the product mixtures was measured with an Anton Parr DMA-35N density meter. Heat of combustion and elemental analyses were conducted under standard protocols by Southwest Research Institute.

α- and β-pinene have net heats of combustion of 132,300 and 132,500 BTU/gal respectively as calculated based on the experimental heat of formation as reported on http://webbook.nist.gov and by others (Hawkins, J. E.; Eriksen, W. T. *J. Am. Chem. Soc.* 1954 76, 2669 and Cox, J. D.; Pilcher, G. *Thermochemistry of Organic and Organometallic Compounds* Academic Press, New York 1970). In comparison the net heat of combustion of JP-10 is 142,000 BTU/gal (Table 3) (Burdette, G. W.; Lander, H. R.; McCoy, J. R. *J. Energy* 1978, 2, 289-292). It should be noted that both pinene molecules also have positive gas phase heats of formation due to strain energy. A path to improving the volumetric heating value of these natural products is selective dimerization that would both increase the density and maintain the ring strain of these molecules. Two target dimer molecules are shown in Diagram 3. Semi-empirical calculations for both of these molecules give positive gas phase heats of formation and impressive values for net heat of combustion (based on a density of 0.94 g/mL); 146,900 BTU/gal and 146,500 BTU/gal for the hypothetical hydrogenated α- and β-pinene dimers, respectively. The gas phase data was calculated utilizing MOPAC, while a liquid phase net heat of combustion was calculated assuming a density of 0.94 g/mL and utilizing double the value of the heat of vaporization of β-pinene according to Hawkins and Armstrong (Hawkins, J. E.; Armstrong, G. T. *J. Am. Chem. Soc.* 1954 76, 3756). These calculations clearly suggest that dimerized pinenes have the potential to have heating values exceeding that of JP-10.

TABLE 3

Selected properties of JP-10 and α- and β-pinene

|  | β-pinene | α-pinene | JP-10 |
|---|---|---|---|
| Density | 0.859 | 0.858 | 0.94 |
| $\Delta H_f(g)$ (kJ/mole) | 35.8 | 30.2 | −96.6[a] |
| $\Delta H_f(l)$ (kJ/mole) | −7.66 | −16.4 | −133.8[b] |
| $\Delta H_c$(BTU/gal)[c] | 132,500[d] | 132,300[d] | 142,000 |

[a]semi-empirical calculation (MOPAC AIM1).
[b]calculated from the experimental heat of combustion.
[c]net heat of combustion.
[d]calculated from the experimental heat of formation.

Diagram 3. Structures of target dimer molecules and selected calculated properties

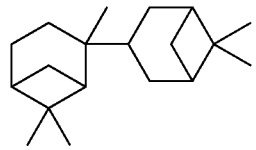

Hydrogenated α-pinene dimer

Calculated $\Delta H_f(g)$ = 48.6 kJ/mol
Calculated $\Delta H_f(l)$ = 44.6 kJ/mol
Calculated $\Delta H_c$(net) = 146,900 BTU/gal

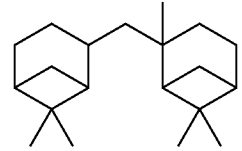

Hydrogenated β-pinene dimer

Calculated $\Delta H_f(g)$ = 4.2 kJ/mol
Calculated $\Delta H_f(l)$ = 82.7 kJ/mol
Calculated $\Delta H_c$(net) = 146,400 BTU/gal Montmorillonite K10

We initially targeted MMT-K10 as a catalyst due to its low cost, abundance, and well established reactivity (Madhavan, D.; Murugalakshmi, M.; Lalitha, A.; Pitchumani, K. *Catalysis Letters* 2001 73, 1). MMT-K10 is a layered aluminosilicate functionalized with sulfonic acid groups through treatment with sulfuric acid. Its acidity can vary several orders of magnitude based on the amount of water present in the sample and it has both Lewis and Bronsted acidic sites (Pillai, S. M.; Ravindranathan, M. *J. Chem. Soc. Chem. Commun.* 1994 1813-1814). The clay can delaminate or separate into particles as little as 1 nm in width and several hundred nanometers in length. Upon addition of MMT-K10 to a flask containing β-pinene at room temperature, a vigorous reaction occurs, with the catalyst immediately turning red accompanied by a rapid exotherm. Without a heat sink, the reaction rapidly reaches the boiling point of β-pinene. In an effort to more effectively control the reaction, slow addition of β-pinene to a slurry of the catalyst in heptane at 0° C. under an inert atmosphere resulted in only a trace amount of isomers (detected by NMR) and no dimers suggesting that the isomerization reaction is very slow at that temperature. Removal of the ice bath led to an exotherm that was controlled by sequentially submerging the rapidly stirred flask in an ice bath and then removing the flask and allowing the internal temperature to warm up to 30 (+/−5)° C. This was repeated several times until the temperature was stable at ambient temperature. At this point the reaction was monitored by both NMR and GC/MS revealing that the principal reaction was isomerization to a mixture of camphene, limonene and α-pinene, with some β-pinene remaining (Scheme 1). Small amounts of dimer, α- and γ-terpinene, and p-cymene were also observed as well as a trace of oxidation products. The relative ratio of α-pinene:camphene: β-pinene:limonene was 3:5:2:4. Heating the mixture to the reflux temperature of heptane led to a vigorous reaction with production of significant amounts of hydrogen. After 1 h the overall yield of dimer molecules was 80% by GC/MS, with the balance of the product represented by primarily p-cymene, camphene, and tricyclene. Extended heating times at the reflux temperature of heptane did not change the concentration of camphene in the reaction mixture, suggesting that MMT-K10 is a poor catalyst for camphene dimerization. Although camphene represents 35% of the initial isomerized product, it represents only about 10% of the final product mixture. This suggests that although MMT-K10 is inefficient for the dimerization of camphene, it does promote the cross coupling of camphene with other isomers in solution. Another important product is p-cymene which is derived from limonene. Previous studies suggest that the mechanism for formation of p-cymene proceeds through a rearrangement/disproportionation reaction in which limonene rearranges to terpinenes which then disproportionate to p-cymene and a menthene such as p-1-menthene (Scheme 2) (Fernandes, C.; Catrinescu, C.; Castilho, P.; Russo, P. A.; Carrott, M. R.; Breen, C. *Applied Catalysis A* 2007 318, 108-120). However, we observed that copious production of hydrogen was evident at the reflux temperature of heptane. This supports a direct dehydrogenative mechanism (Scheme 3) that could be catalyzed by the clay or possibly by polyaromatic coke deposits on the catalyst surface (Arnano, H.; Sato, S.; Takahashi, R.; Sodesawa, T. *Phys. Chem. Chem. Phys.* 2001 3, 873-879).

Scheme 1. Mechanism for the isomerization of β-pinene over MMT-K10

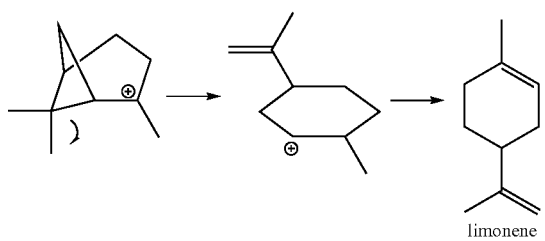

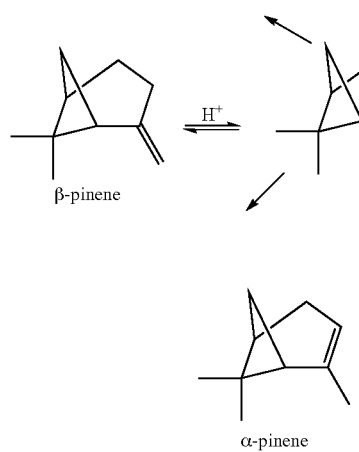

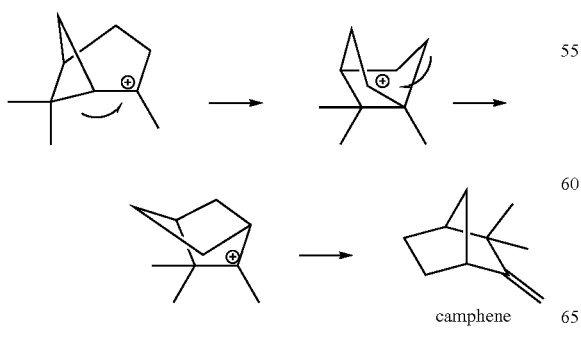

Scheme 2. Potential mechanism for the conversion of β-pinene to *p*-cymene

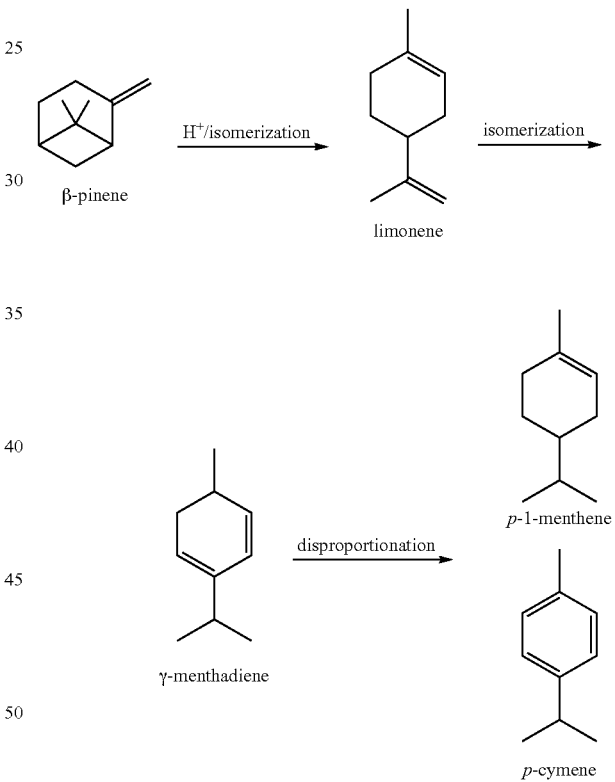

Scheme 3. Potential mechanism for the conversion of β-pinene to *p*-cymene

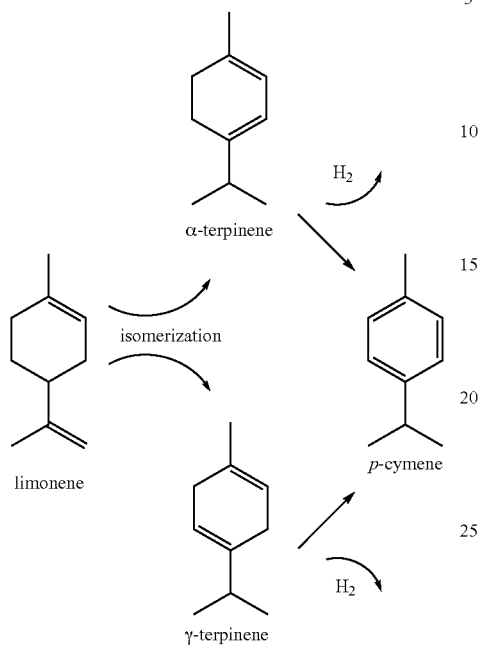

To shed some light on the mechanism, (R)-(+)-limonene was added dropwise to a stirred slurry of MMT in refluxing heptane. After one hour an NMR spectrum was collected and it was observed that limonene, p-cymene, α- and γ-terpinene and terpinolene were the primary low molecular weight components present. This result supports the second mechanism (Scheme 3), given that no evidence was observed for any menthene products. It is also of interest that the intermediate terpinolene was observed in the reaction mixture, suggesting that the isomerization reaction progresses in a step-like fashion (Scheme 4).

Although no menthene products were observed in the NMR spectrum, GC/MS analysis of an MMT limonene mixture in heptanes that had been refluxed overnight revealed the presence of p-cymene and residual menthenes, primarily p-menth-3-ene and p-menth-1-ene. The presence of these particular menthenes was expected based on the carbocationic mechanism of isomerization and the stability of intermediates with tertiary cationic centers. The data suggest that a competition exists between the first and second mechanism, with some disproportionation occurring through a dehydrogenative/hydrogenative mechanism and some direct loss of hydrogen ostensibly due to the slower rate of hydrogenation under these conditions. Additionally, many other potential reactants in solution including dimer molecules could potentially react with the released hydrogen. The GC/MS analysis reveals that the dimer region is a complex mixture of peaks mainly with molecular weights of 272, while some peaks have m/z=274. It is unclear whether the molecule(s) represented by the m/z=274 peaks are produced by hydrogenation after dimerization of two monomers, or if they are produced from the coupling of a monoolefin and a diolefin. A recent report has suggested that under somewhat harsher conditions (150° C., acidic clay catalyst), terpinenes and other olefins undergo a Diels Alder reaction (Scheme 5) that is promoted by the Lewis acidity of the catalyst (Fernandes, C.; Catrinescu, C.; Castilho, P.; Russo, P. A.; Carrott, M. R.; Breen, C. *Applied Catalysis A* 2007 318, 108-120).

Scheme 4. Stepwise conversion of limonene to terpinenes through terpinolene

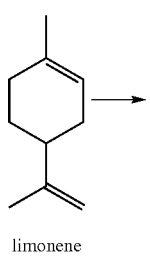

limonene

Scheme 5. Example of a potential Diels Alder dimerization reation of a-terpinene. Similar reaction could occur between terpenines and a variety of olefins in solution.

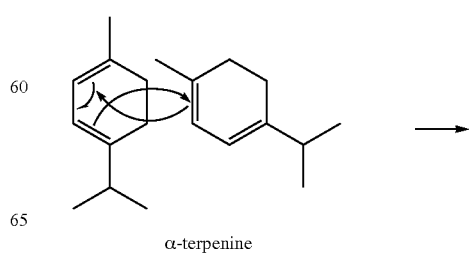

α-terpenine

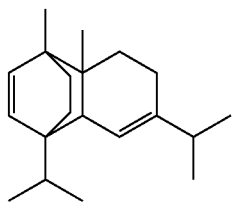

Although the conversion to p-cymene is of interest, it limits the conversion of β-pinene to dimer products. In an attempt to efficiently control the heat of reaction and to selectively produce dimers incorporating ring strained cyclobutane rings, β-pinene was added dropwise to a stirred slurry of MMT-K10 in refluxing heptane under a nitrogen atmosphere. Upon addition of the first drop the slurry turned green and then rapidly converted to a red/brown suspension. After the addition, the mixture was refluxed for an additional hour. Interestingly, the NMR spectra and GC-MS chromatograms were indistinguishable from those obtained when β-pinene was added slowly at room temperature and then heated to refluxing heptane temperatures. This result suggests that the rate of isomerization at the elevated temperature is faster than the rate of dimerization of β-pinene. To determine the effect of even higher temperatures, β-pinene was added neat to the clay catalyst in an open flask maintaining a slow flow of nitrogen. The mixture was vigorously stirred and rapidly rose in temperature until vigorous gas evolution was evident. After the bubbling had mostly subsided, the flask was placed in an oil bath at 150° C. and further evolved gas was allowed to slowly escape through a bubbler. The distribution of products was similar to that observed at 100° C. with the addition of about 10% trimer, leading to a 70/10/20 ratio for dimer/trimer/low molecular weight products. This result suggests that the intermediate temperature is ideal, leading to a high conversion to dimer while limiting the formation of trimer or other heavier oligomers. The clay catalyst can be removed with some difficulty from the reaction mixture by filtration, however as the catalyst is remarkably well dispersed it was often more convenient to separate the clay by centrifugation followed by decantation.

Amberlyst-15

Although MMT-K10 was found to be an efficient dimerization catalyst, in an attempt to produce a dimer mixture with less isomerized products and more molecules maintaining strained ring systems, Amberlyst-15, a sulfonic acid functionalized cross-linked polystyrene resin was investigated to determine its catalytic activity for the dimerization of β-pinene. Unlike MMT-K10, upon addition of neat β-pinene to beads of Amberlyst-15 under nitrogen, no reaction at room temperature occurred even upon reaction times of 48 hours. This difference in activity may be due to the presence of Lewis acidic sites present in MMT-K10 which may allow for coordination and isomerization of β-pinene at low temperature (Fernandes, C.; Catrinescu, C.; Castilho, P.; Russo, P. A.; Carrott, M. R.; Breen, C. *Applied Catalysis A* 2007 318, 108-120). Upon heating to 140° C. for 3 h, a mixture of primarily β-pinene and camphene were present with traces of p-cymene and dimer. Given the slow reaction rate, negligible conversion to dimer and high reaction temperature, Amberlyst-15 was not studied in further detail.

Nafion®

Nafion® is a sulfonated tetrafluoroethylene based fluoropolymer-copolymer incorporating perfluorovinyl ether groups terminated with sulfonate groups onto a tetrafluoroethylene (Teflon) backbone, and may be considered to be a perfluorinated sulfonic acid resin. The combination of fluorinated backbone, sulfonic acid groups, and the stabilizing effect of the polymer matrix render Nafion® a very strong acid (i.e., superacid), with $pK_a$ about −6. Nafion® has various chemical configurations and thus several chemical names, including: ethanesulfonyl fluoride, 2-[1-[difluoro-[(trifluoroethenyl)oxy]methyl]-1,2,2,2-tetrafluoroethoxy]-1,1,2,2,-tetrafluoro-, with tetrafluoroethylene; and, tetrafluoroethylene-perfluoro-3,6-dioxa-4-methyl-7-octenesulfonic acid copolymer, for example. Nafion® is of course insoluble. It will be clear to those of skill in the art that polyacidic or heteropolyacidic clays other than MMT-K10, and perfluorinated sulfonic acid resins other than Nafion® NR50 may be suitable to facilitate the synthesis of pinene dimers, and the use of such other catalysts in the synthetic schemes disclosed are within the scope of this disclosure. For convenience in discussion, we refer herein to the sulfonated tetrafluoroethylene based fluoropolymer-copolymer incorporating perfluorovinyl ether groups terminated with sulfonate groups class of catalysts, suitable for use in synthesis of β-pinene dimer, including the Nafion® catalysts, as well as the acidic clays, simply as solid heterogeneous acidic catalysts or solid heteropolyacidic catalysts.

Diagram 4. Structure of Perfluorinated Sulfonic Acid Resin Catalysts

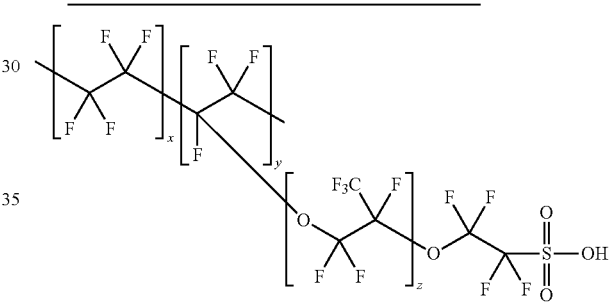

With respect to the catalysts of the structure shown in Diagram 4, the variables x, y, and z are mutually independent integers greater than 1. That is, any one of the variables x, y, z may have an integer value which is not dependent on the value of any other variable.

Unlike MMT-K10 which maintains a high surface area and can delaminate at elevated temperature to yield easily dispersible nanosized catalyst particles, Nafion naturally does not disperse well in non-polar solvents (Botella, P.; Corma, A.; López-Nieto, J. M. *J. Catal.* 1999 185, 371-377). This limits the surface area of the catalyst and the relative amount of active sites in contact with the reaction medium. Nafion can be well dispersed on inorganic supports including silica or alumina, but the presence of the support can often influence the reactivity and in the case of β-pinene may lead to isomerization products and lower ring strain dimers (Kumar, P.; Vermeiren, W.; Dath, J.; Hoelderich, W. F. *Energy Fuels* 2006 20, 481-487). The catalyst was prepared by precipitation of a Nafion dispersion from water/alcohol and was dried under vacuum (4 mmHg) at ambient temperature to yield a flocculent white powder. In a manner similar to Amberlyst-15, Nafion showed virtually no reaction at room temperature for reaction times as long as 24 h. When neat solutions of β-pinene were heated with Nafion to 90° C. with stirring, no reaction occurred for an extended period of time, typically 20-50 minutes, and then without warning, the Nafion turned a dark red color and a rapid exothermic reaction ensued with evolution of gas. Upon an additional hour at 90° C., ¹H NMR spectroscopy revealed that the only remaining low molecular weight molecules were camphene and a small amount of p-cymene. In fact when MMT-K10 was used as a catalyst nearly 10 times more p-cymene was produced. This result suggested that either the ring opening mechanism that converts β-pinene to limonene does not readily occur with Nafion at these reaction temperatures, or that the rate of dimerization of limonene over Nafion is substantially faster than the dehydrogenation reaction to produce p-cymene. To differentiate between the two possibilities, a reaction was stopped prior to completion and an NMR spectrum was collected. Camphene was the dominant monomeric olefin, with small, nearly equal amounts of β-pinene and limonene. At this point in the reaction, p-cymene was not observed in the ¹H NMR spectrum. It appears from the data that the primary mechanism over Nafion is conversion to camphene concomitant with homo- and cross-dimerization of the olefin mixture. Upon further reaction it was observed that the last olefin remaining is camphene which dimerizes somewhat sluggishly over Nafion, however, unlike MMT-K10, continued reaction at 100° C. led to the conversion of camphene to dimer molecules. In order to determine the effect of temperature, the reaction was run neat at 140° C. using Nafion as the catalyst. Interestingly, p-cymene was formed in amounts similar to that observed for MMT-K10, in addition to the observance of about 10 wt % trimer. This suggests that for Nafion the dehydrogenation of limonene to p-cymene is favored at higher temperatures, while dimerization is favored at lower/intermediate temperatures. As with MMT-K10, it appears that a temperature of 100° C. is ideal for maximizing the amount of dimer produced. For all of the Nafion reactions, the catalyst could be removed by simple decantation and reused at least 3 times without significant loss of activity and given sufficient reaction time, yields of dimer as high as 90% were obtained. As mentioned previously, at the conclusion of the reaction the Nafion takes on a deep red hue. Washing the Nafion 5 times with $CH_2Cl_2$ did not remove the color, but only weak C—H stretches were observed in the IR spectrum of the washed and dried catalyst. With respect to FIG. 1, the GC/MS chromatogram of the product mixture revealed a broad distribution of dimer molecules with the majority having m/z=272. Small amounts of other molecular weights such as 274 and 288 were also observed, with the former being attributed to the coupling of terpinenes and menthenes and the latter attributed to isobornyl ether which has been shown to be an oxidation product produced from camphene with heteropolyacidic catalysts (Scheme 6) (Lana, E. J. L.; da Silva Rocha, K. A.; Kozhevnikov, I. V.; Gusevskaya, E. V. *J. Molec. Catal. A* 2006 243, 258-263).

Upgrading of Dimer Mixtures

The dimer yield varied depending on the catalyst and conditions. Yields of dimer were reduced when MMT-K10 was utilized due to an increase in the amount of p-cymene produced and the inability of MMT-K10 to efficiently homodimerize camphene. The amount of dimer was also heavily influenced by the reaction temperature in that higher temperatures produced trimer molecules and potentially other higher oligomers. Reactions run at greater than 140° C. produced colored solutions ranging from dark yellow to orange-red depending on the reaction time, suggesting that polymeric or conjugated mixtures were being produced. Reactions controlled at about 100° C. with refluxing heptanes gave colorless mixtures when MMT-K10 was utilized as the catalyst and pale yellow mixtures when Nafion was utilized.

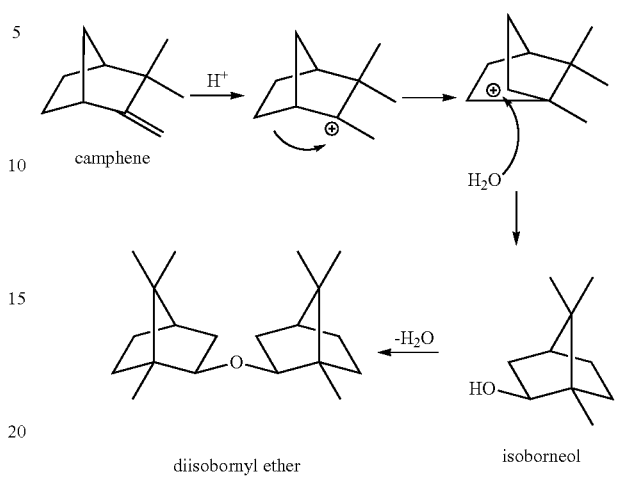

Scheme 6. Acid catalyzed conversion of camphene to diisobornyl ether

For potential use as fuels, these dimer mixtures must be hydrogenated to increase their stability. The reaction mixtures were simply decanted and transferred to another flask for hydrogenation; no workup or caustic treatment was required. Platinum dioxide ($PtO_2$) was utilized as the hydrogenation catalyst under mild $H_2$ pressures as it has been shown to be a very efficient hydrogenation catalyst for hindered olefins (Wright, M. E.; Harvey, Benjamin G.; Quintana, R. *Energy and Fuels* 2008, 22, 3299) (Harvey, B. G.; Wright, M. E.; Quintana, R. L. *Preprints of Symposia-ACS Div. Fuel Chem.* 2009 54 305-306). The resulting dimer mixtures were then placed under reduced pressure to remove n-heptane and low molecular weight products including camphane (MMT-K10 catalyst) and then vacuum distilled to produce a dimer cut. Fractional vacuum distillation gave a trace of a low boiling fraction consisting of primarily camphane, and p-cymene, followed by a colorless dimer fraction (bp 116-122° C., 4 mmHg) and leaving a small amount of resinous solid pot residue comprising a mixture of dimer and traces of other heavier oligomers. Isolated, distilled yields of the dimer fraction were greater than 80% on a 30 g scale, while for larger operations, a yield of up to 90% based on the GC/MS data seems reasonable due to more efficient distillations. Although higher oligomers limit the yield of dimer molecules they have uses in a variety of industries as resins and glues (Goldschmidt, S.; McBride, J. J. *in Polymeric Materials Encyclopedia* Vol. 9; Salamone, J. C. Ed. CRC Press 1996 6878-6884). The properties of the fuel are listed in Table 3. The density of the hydrogenated dimer mixture prepared with Nafion was 0.938 g/cm³, similar to JP-10 at 0.94 g/cm³. The net heat of combustion of the dimer mixture was 141,745 BTU/gal, virtually identical to JP-10 (142,000 BTU/gal), while the pour point was determined to be −30° C., substantially higher than JP-10 with a freezing point of −79° C.

TABLE 3

Selected Properties of Hydrogenated Pinene Dimers

| Property | Value |
|---|---|
| Density, g/cm³ | 0.938 |
| Heating Value, MJ/L | 39.5 |
| (BTU/gal) | 141,745 |

TABLE 3-continued

Selected Properties of Hydrogenated Pinene Dimers

| Property | Value |
|---|---|
| Pour Point, ° C. | −30 |
| Sulfur, ppm | 0.5 |
| Carbon, % | 87.72 (calc. for $C_{20}H_{34}$: 87.52) |
| Hydrogen, % | 12.12 (calc. for $C_{20}H_{34}$: 12.48) |

While what are presently considered to be the most practical and preferred embodiments have been described, it is to be understood that the invention is not to be limited to the disclosed embodiments, but to the contrary, is intended to cover various modifications, embodiments, and equivalent processes included within the spirit of the invention as may be suggested by the teachings herein, which are set forth in the appended claims, and which scope is to be accorded the broadest interpretation so as to encompass all such modifications, embodiments, and equivalent processes.

What is claimed is:

1. A process for making a high density fuel comprising:
providing a catalytic amount of a first catalyst selected from one of a montmorillonite polyacidic clay or a perfluorinated sulfonic acid resin;
slurring said first catalyst in hexane under a nitrogen atmosphere;
adding β-pinene incrementally to said slurry with stirring to form a first reaction mixture;
heating said first reaction mixture to about 100° C.;
stirring the heated first reaction mixture until reaction of reactants is substantially complete to form a second reaction mixture;
removing the first catalyst from the second reaction mixture;
adding a platinum dioxide hydrogenation catalyst to the second reaction mixture under a hydrogen atmosphere;
stirring the second reaction mixture to allow contact of reactants until reaction of reactants is substantially complete to form a third reaction mixture containing hydrogenated α-pinene dimer and hydrogenated β-pinene dimer;
removing the activated platinum dioxide catalyst from the third reaction mixture;
removing the hexane from the third reaction mixture to form a residue; and
isolating said hydrogenated α-pinene dimer and hydrogenated β-pinene dimer from the residue to form a high density fuel.

2. The process of claim 1 wherein the montmorillonite polyacidic clay is MMT-K10.

3. The process of claim 1 wherein the perfluorinated sulfonic acid resin has the structure represented by (A),

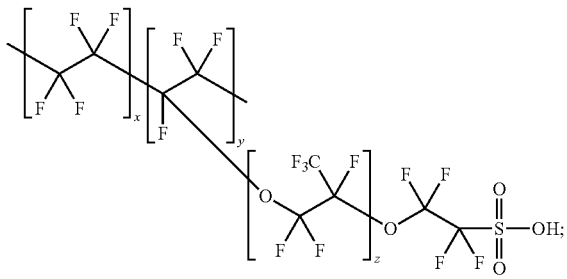

(A)

wherein x, y, and z are mutually independent integers greater than 1.

* * * * *